United States Patent [19]

Munekawa

[11] Patent Number: 4,972,448
[45] Date of Patent: Nov. 20, 1990

[54] GONIOMETER IN AN X-RAY DIFFRACTION DEVICE

[75] Inventor: Shigeru Munekawa, Tokyo, Japan

[73] Assignee: Rigaku Denki Kabushiki Kaisha, Tokyo, Japan

[21] Appl. No.: 299,584

[22] Filed: Jan. 23, 1989

[30] Foreign Application Priority Data

Jan. 22, 1988 [JP] Japan .................................. 63-10763

[51] Int. Cl.⁵ ............................................. G01N 23/20
[52] U.S. Cl. ......................................... 378/81; 378/79
[58] Field of Search .................... 378/87, 79, 70, 71

[56] References Cited

U.S. PATENT DOCUMENTS 3,870,880  3/1975  Meriqoux et al. ..................... 378/87
4,263,510  4/1987  Ciccarelli et al. ..................... 378/87

FOREIGN PATENT DOCUMENTS 1040390  7/1983  U.S.S.R. ................................ 378/87

Primary Examiner—Carolyn E. Fields
Assistant Examiner—David P. Porta
Attorney, Agent, or Firm—Sughrue, Mion, Zinn, Macpeak and Seas

[57] ABSTRACT

A goniometer in an X-ray diffraction device comprises a sample table rotatably provided about a center axis of a sample for holding a sample, an X-ray source rotatably provided about the center axis of the sample for irrdiating first X-ray onto a sample, and an X-ray detector rotatably provided about the center axis of the sample for detecting second X-rays resulting from the irradiation of the first X-rays, the second X-rays being diffracted X-rays depending upon a sample. The sample table, the X-ray source an the X-ray detector are rotatable independently of one another, and a component to be fixed can be freely selected in accordance with a purpose of measurement and sample attachments employed. As such, various kinds of measuring methods are available to perform X-ray diffraction analysis by a single goniometer.

2 Claims, 4 Drawing Sheets

GONIOMETER IN AN X-RAY DIFFRACTION DEVICE

BACKGROUND OF THE INVENTION

The present invention relates to a goniometer in an X-ray diffraction device, and more particularly to an improvement of a goniometer which is used in conjunction with an X-ray diffraction device, such as a diffractometer.

An X-ray diffraction device, such as a diffractometer, has been used for X-ray diffraction analysis. In X-ray diffraction analysis by the diffractometer, a crystal structure of a substance, for example, is analyzed by irradiating an X-ray onto the substance and measuring a diffraction angle of the X-ray reflected from or passed through the substance. A goniometer is employed in conjunction with the diffractometer for measuring a diffraction angle of the X-ray.

Next, a basic structure of a conventional goniometer will be described with reference to FIG. 12.

The goniometer comprises an X-ray source 60, a receiving slit 61, X-ray detector 62, and a sample table for holding a sample 63. The X-ray source 60 and the receiving slit 61 are disposed so that the distance L1 between the X-ray source 60 and the sample 63 is equal to the distance L2 between the receiving slit 61 and the sample 63. Therefore, the X-ray source 60 and the receiving slit 61 are always positioned on a predetermined circle 64 having a radius of L1 (=L2) which is drawn around a center axis 0 of the sample 63. The predetermined circle 64 is referred to as the diffractometer circle. The goniometer is classified into two types depending upon the plane in which its diffractometer circle is included, one of which is of a lateral type having the diffractometer circle in a horizontal plane, the other of which is of a vertical type having the diffractometer circle in a vertical plane.

In the goniometer, in order to change an incident angle ($\theta$) of the X-ray with respect to a lattice plane of a sample, it is necessary to change a relative position between the X-ray source 60 and the sample 63. In accordance with the change of the relative position therebetween, it is further necessary to change a relative position between the receiving slit 61 and the sample 63 so that the diffracted X-ray is received in the receiving slit 61. Accordingly, in the conventional goniometer, two selected arbitrarily from the X-ray source 60, the sample 63 and the receiving slit 61 are made to be rotatable about the center axis 0 of the sample 63 while unrotatably fixing the remainder. Depending upon the component unrotatably fixed, the goniometer is classified into three types; the X-ray source fixed type (referred to as $\theta$–$2\theta$ operation system) in which the X-ray source is unrotatably fixed, the sample table fixed type (referred to as $\theta$—$\theta$ operation system) and the receiving slit fixed type (or the X-ray detector fixed type). These three types of goniometers are applicable to both the lateral and vertical types of goniometers aforementioned. In general, employed are the X-ray source fixed and the lateral type goniometer, the X-ray source fixed end the vertical type goniometer, and the sample fixed and the vertical type goniometer. Particularly the sample horizontally fixed and the vertical type is referred to as a horizontal type goniometer.

In the conventional goniometer, any one of the X-ray source, the sample and the X-ray detector disposed adjacent the receiving slit is unrotatably fixed. Selection of the component to be unrotatably fixed is determined on the basis of intended advantages. However, each of the three unrotatably fixed manners may inherently provide disadvantages. That is, the X-ray source fixed type has a disadvantage in that a heavy weight structure is not applicable to both the sample table and the X-ray detector because of necessity of their rotation. Therefore, attachments of heavy weight, such as high pressure vessel, cannot be provided on the sample table. Further, an X-ray detector of heavy weight, such as a solid state detector, cannot be utilized. On the other hand, in the X-ray source fixed type, a large scale X-ray source cannot be used because of the necessity of its rotation.

SUMMARY OF THE INVENTION

The present invention has been made in view of the foregoing disadvantages, and accordingly, it is an object of the present invention to provide a goniometer in which a sample table, an X-ray source and an X-ray detector are made to be rotatable independently of one another, such that the component to be fixed can be freely selected in accordance with a purpose of measurement and sample attachments attached to the components, such as a sample table.

In order to achieve the foregoing and other objects, according to the present invention, there is provided a goniometer in an X-ray diffraction device for irradiating first X-rays onto a sample and detecting second X-rays resulting from the irradiation of the first X-rays, the second X-rays being diffracted depending upon a sample, and a sample having a center axis, the goniometer comprising: a sample table rotatably provided about the center axis of the sample for holding the sample; an X-ray source rotatably provided about the center axis of the sample for irradiating the first X-rays onto the sample; an X-ray detector rotatably provided about the center axis of the sample for detecting the second X-rays. According to the present invention, since the sample table, the X-ray source and the X-ray detector are rotatable independently of one another, a component to be fixed can be freely selected in accordance with a purpose of measurement and sample attachments employed, various kinds of measuring methods are available to perform X-ray diffraction analysis by a single goniometer.

DETAILED DESCRIPTION OF THE PREFERRED EMBODIMENTS

Figure 1:
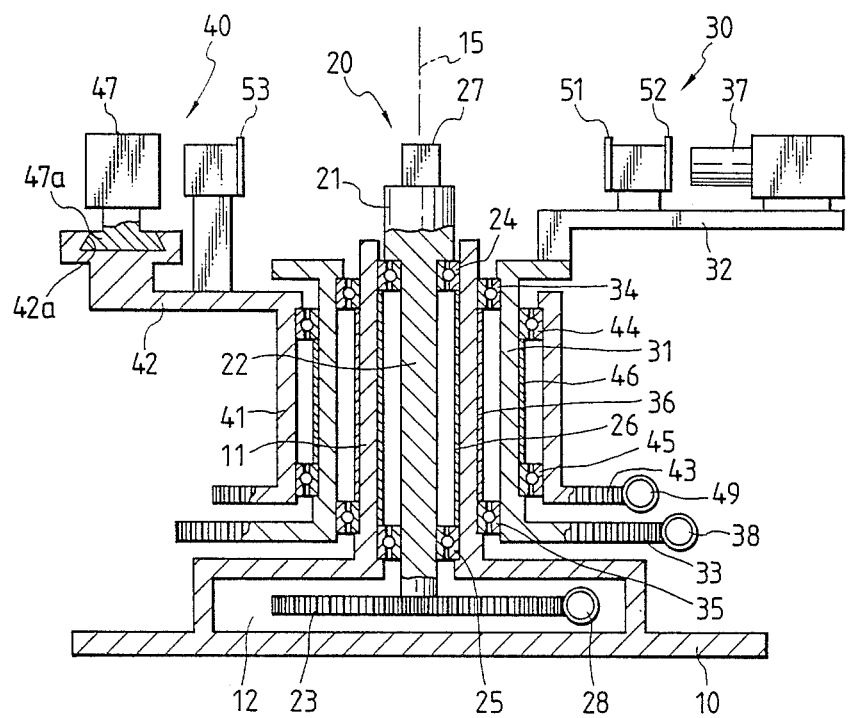
Fig. 1 is a cross-sectional view showing a goniometer in an X-ray diffraction device according to one embodiment of the invention.

FIG. 1 illustrates a lateral type goniometer according to one embodiment of the invention.

A goniometer comprises a base plate 10, a sample table unit 20, an X-ray detector unit 30 and an X-ray tube unit 40. The units 20 and 30 are assembled together through the bearings 34, 35 interposed therebetween, end the units 30 and 40 are assembled together through the bearings 44, 45. The base plate is integral with a cylindrical member 11. The cylindrical member 11 has a large-diameter portion and a small-diameter portion, and an open end of the former is integral with the base plate 10. The interior of the cylindrical member 11 defines a space 12 for accommodating a shaft 22 and a wormwheel 23.

Figure 2:
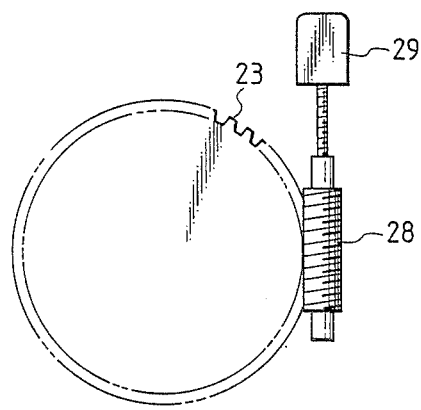
FIG. 2 is a plan view showing a driving mechanism for rotating a sample table.

The sample table unit 20 includes a sample table 21 for holding a sample, the shaft 22 extending vertically and supported by the cylindrical member 11 through bearings 24, 25, and the wormwheel 23 fixedly secured to the lower end of the shaft 22 and accommodated within the space 12. A spacer 26 is interposed between the two bearings 24,25. A sample plate 27 is detachably mounted on the sample table 21. The wormwheel 23 is in meshing engagement with wormgear 28 connected to a pulse motor 29 as shown in FIG. 2.

The X-ray detector unit 30 includes a hollow shaft 31 extending vertically and supported by the cylindrical member 11 through bearings 34,35, a supporting arm 32 horizontally extending and mounted on the upper end of the hollow shaft 31 end a wormwheel 33 fixedly secured to the lower end of the shaft 31. A spacer 36 is interposed between two bearings 34,35. An X-ray detector 37 is mounted on the supporting arm 32. A receiving slit 51 and a scatter slit 52 are disposed adjacent the X-ray detector 37 on the supporting arm 32. The wormwheel 33 is in meshing engagement with a wormgear 38 connected to a pulse motor (not shown) in the same manner as shown in FIG. 2.

The X-ray tube unit 40 includes a hollow shaft 41 extending vertically and supported by the hollow shaft 31 through bearings 44, 45, a supporting arm 42 integrally provided on the upper end of the hollow shaft 41, and a wormwheel 43 fixedly secured to the lower end of the shaft 41. A spacer 46 is interposed between two bearings 44,45. An X-ray tube 47 is slidably movable provided on the supporting arm 42. That is, the supporting arm 42 is formed with a groove 42a extending in a direction perpendicular to the sheet of drawing, the X-ray tube 47 has a lower end portion 47a engaged with the groove 42a. Therefore, the X-ray tube 47 is moved along the longitudinal direction of the groove 42a by the activation of a pulse motor (not shown). A divergence slit 53 is disposed adjacent the X-ray tube 47 on the supporting arm 42. The wormwheel 43 is in meshing engagement with a wormgear 49 connected to a pulse motor (not shown) in the same manner as shown in FIG. 2.

With this arrangement, X-rays generated from the X-ray tube 47 pass through the divergence slit 53 which limits their divergence. The X-rays are incident upon a sample on the sample table 27, diffracted X-rays reflected therefrom are detected and processed by the X-ray detector 37 after passing through the receiving slit 51 and the scatter slit 52. The receiving slit 81 serves to limit the X-rays entering the X-ray detector 37, the scatter slit 52 serves to interrupt and prevent the scattering X-rays from entering the X-rays detector 37. Only the X-ray from the sample are allowed to enter the X-ray detector 37. In this X-ray diffraction analysis, when the wormgears 38 and 49 are driven, the X-ray tube 47 provided on the hollow shaft 41 and the receiving slit 51 provided on the hollow shaft 31 are independently rotated about the center axis 15 of the sample on the diffractometer circle. The X-ray detector 37 is rotated about the center axis 15 of the sample together with the receiving slit 51. The sample table 27 is further independently rotatable about the center axis 15 by driving the wormgear 28. That is, the sample table 21, X-ray detector 37 and X-ray tube 47 are rotatable about the center axis 15 in the goniometer independently of one another.

Next, several methods of using the goniometer thus constructed will be described below with reference to FIGS. 3 through 9.

FIGS. 3 through 9 are plan views showing the relationship of relative position among X-rays 54 generated from the X-ray tube 47, the sample 55 on the sample table and the X-ray detector 37, any other components are not shown. These figures illustrate the lateral type goniometer, in case of the vertical type goniometer, FIGS. 3 through 9 can be seen as front views in place of plan views. In FIGS. 3 through 9, $\theta s$ represents a rotational angle of the X-ray tube 47, $\theta c$ a rotational angle of the sample table 21, and $\theta d$ a rotational angle of the X-ray detector 37.

Figure 3:
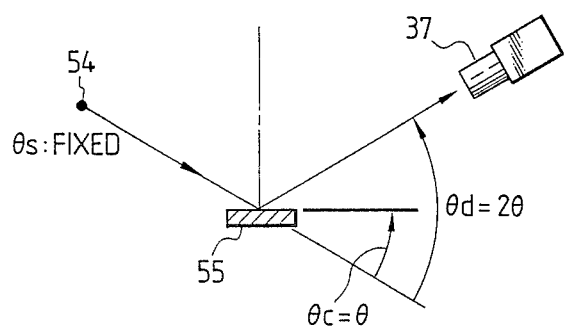
FIGS. 3 through 9 are plan views showing methods of using a goniometer in an X-ray diffraction device according to one embodiment of the invention.

A. In case of the X-ray tube fixed:

The X-ray tube, namely, the X-rays 54 is fixed, and thus the rotational angle $\theta s$ of the X-ray tube is unchangeable. In this case, an angular velocity of the X-ray detector 37 is set to be twice as large as that of the sample 55, that is, when the rotational angle $\theta c$ of the sample table is $\theta$, the rotational angle $\theta d$ of the X-ray detector becomes equal to $2\theta$ as shown in FIG. 3. This arrangement of the goniometer is same as that of the conventional lateral goniometer.

Figure 4:
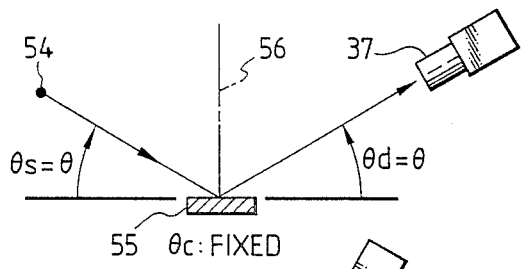

B. In case of the sample table fixed:

The sample table is fixed, and thus the rotational angle of the sample is unchangeable. The reference numeral 56 designates a normal line of the lattice plane to be measured. In this case, an angular velocity of the X-ray tube 47 is set to be equal to that of the X-ray detector 37, that is, when the rotational angle $\theta s$ of the X-ray tube is $\theta$, the rotational angle $\theta d$ of the X-ray detector becomes equal to $\theta$ as shown in FIG. 4. Since this arrangement of the goniometer includes the sample table fixed, attachments of heavy weight, such as high pressure vessel, can be provided on the sample table. The sample can be held horizontally, if this arrangement is applied to the vertical type goniometer.

Figure 5:
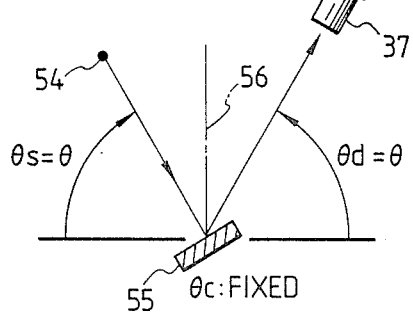

FIG. 5 shows another method of using the sample table fixed type goniometer. In this method the lattice plane to be measured is inclined with respect to a surface of the sample 55. Strain in the sample 55 may be observed and measured by performing X-ray diffraction analysis in a state in which inclination degree of the sample 55 is changed. That is, when the sample 55 is subject to external load, such as a tensile load, a lattice plane interval becomes longer or shorter depending on directions, for example, in case the tensile load is applied to the sample 55, there exists not only an axial strain which causes elongation in the tensile direction, but also a lateral strain which causes shrinkage in a direction perpendicular to the tensile load. The strain in a direction selected arbitarily among these strains may be measured by the method as shown in FIG. 5.

Figure 6:
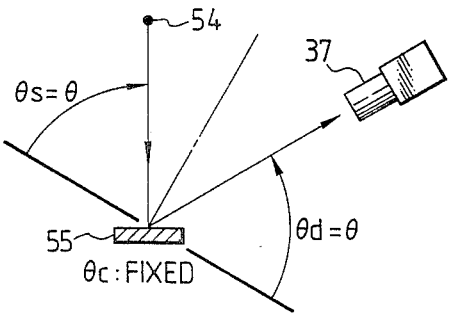

FIG. 6 shows still another method of using the sample table fixed type goniometer. In this method, the lattice plane to be measured is also inclined with respect to a surface of the sample 55. Only one difference between the methods shown in FIGS. 5 and 6 is that the sample is fixed without inclination.

Figure 7:
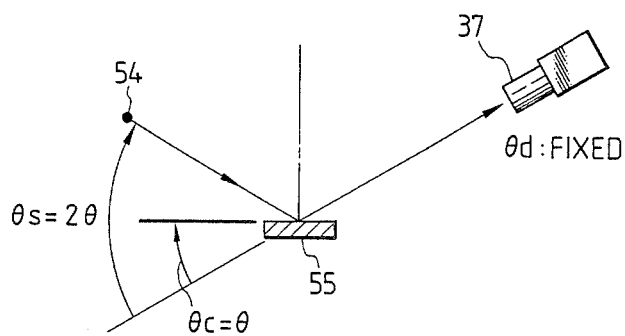

C. In case of the X-ray detector fixed:

In this case, the X-ray detector is fixed, and thus the rotational angle of the X-ray detector is unchangeable. An angular velocity of the X-ray tube 47 is set to be twice as large as that of the sample table 27, that is, when the rotational angle $\theta c$ of the sample table is $\theta$, the rotational angle $\theta s$ of the X-ray tube becomes equal to $2\theta$ as shown in FIG. 7. Since this arrangement of the goniometer includes the X-ray detector 37 fixed, the X-ray detector 37 of heavy weight, such as a solid state detector, can be utilized.

Figure 8:
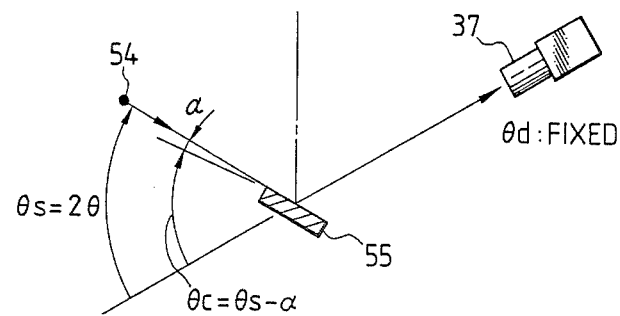

FIG. 8 shows another method of using X-ray detector fixed type goniometer. In this method, when the rotational angle $\theta s$ of the X-ray tube is equal to $2\theta$, the rotational angle $\theta c$ of the sample table becomes equal to $\theta s - \alpha$. Accordingly, the X-rays 54 are incident upon the sample 55 at an angle $\alpha$ with respect to the surface of the sample. This method is employed to perform X-ray diffraction analysis for a film-like sample, since small incident angle allows X-rays to travel for a long distance in the film-like sample. The incident angle is usually adjusted to be in the range of 2 to 5 degrees.

Figure 9:
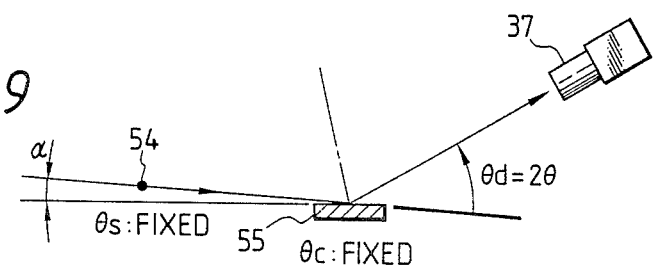

D. In case of the X-ray tube fixed and the sample table fixed:

In this case, both the X-ray tube and the sample table are fixed, and thus the rotational angle $\theta s$ of the X-ray tube and the rotational angle $\theta c$ of the sample are set to be unchanged as shown in FIG. 9. This method is also applicable to measure film-like sample similar to the method shown in FIG. 8. The X-rays 54 and the sample 55 are fixed so that the X-rays 54 are incident upon the sample 55 at an angle $\alpha$ with respect to the surface of the sample. And the X-ray detector 37 is rotatable about the center axis of the sample 55.

As will be apparent from the aforementioned description, according to this goniometer, various measuring methods are available to samples, a measuring method can be freely selected in accordance with a purpose of measurement and sample attachments employed.

Next, the goniometer is interchangeably used either as a lateral type or a vertical type, which will be described with reference to FIGS. 10 and 11.

Figure 10:
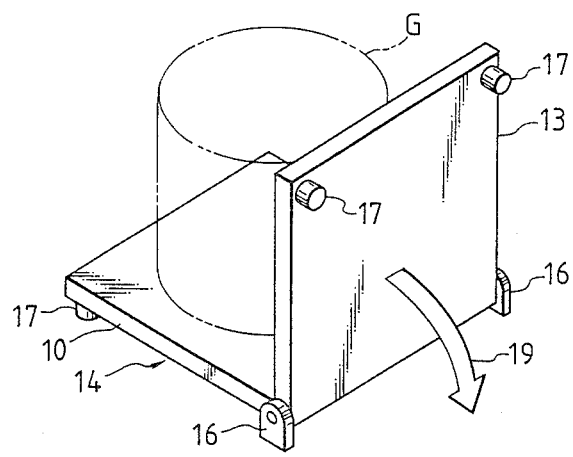
FIGS. 10 and 11 are perspective views showing another embodiment of the invention.
Figure 11:
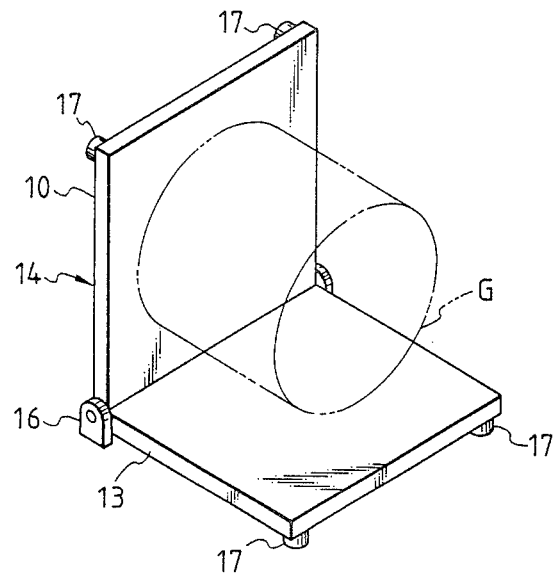
Figure 12:
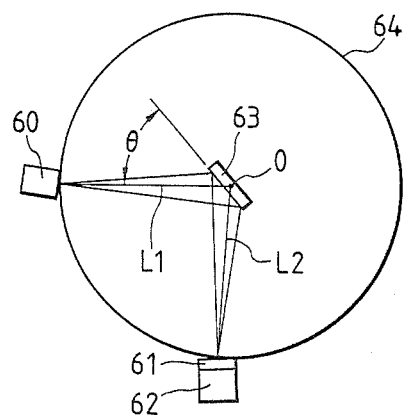
FIG. 12 is an explanatory diagram showing a conventional goniometer.

In FIG. 10, a base plate unit 14 comprises a base plate 10 and a side plate 13 vertically extending and fixedly provided on the base plate 10 with a hinge 16. The base plate 10 and the side plate 13 have two legs 17,17 at positions apart from the hinge 16, respectively.

The goniometer G is shown by phantom lines on account of simplicity of drawings. The lateral type goniometer as shown in FIG. 10 can be used as the vertical type goniometer as shown in FIG. 11. That is, the base plate unit 14 is rotated by 90 degrees as indicated by an arrow 19, to thereby locate the base plate 10 holding the goniometer G vertically. With reverse rotation, the vertical type goniometer can be used as the lateral type goniometer.

In view of the foregoing, according to the present invention, since a sample table, an X-ray source and an X-ray detector are independently rotatably provided, a component to be fixed can be freely selected in accordance with a purpose of measurement and sample attachments employed. Various kinds of measuring methods are thus available to perform X-ray diffraction analysis by a single goniometer. If, for example, the X-ray source and the X-ray detector are rotatable and the sample table is fixed, attachments of heavy weight, such as high pressure vessel, can be provided on the sample table. If both the sample table and the X-ray source are set to be rotatable while fixing the X-ray detector, the X-ray detector of heavy weight, such as a solid state detector, can be utilized.

Further, according to the present invention. a lateral type goniometer and a vertical type goniometer are interchangeably used with a single goniometer, since position of a support member holding the goniometer is interchangeable between a vertical position and a horizontal position.

What is claimed is:

1. A goniometer for X-ray diffraction analysis, comprising:
   (a) a base plate (10),
   (b) a hollow cylindrical support member (11) extending outwardly from the base plate and perpendicular thereto,
   (c) a shaft (22) rotatably journalized in the support member,
   (d) a sample table (21) provided on one end of the shaft, remote from the base plate,
   (e) a first wormwheel (23) provided on another, opposite end of the shaft,
   (f) a first support cylinder (31) surrounding the support member and rotatably journalled thereon,
   (g) a first support arm (32) extending radially outwardly from one end of the first support cylinder, remote from the base plate, and mounting an X-ray detector unit (30),
   (h) a second wormwheel (33) provided on another, opposite end of the first support cylinder,
   (i) a second support cylinder (41) surrounding the first support cylinder and rotatably jounalled thereon,
   (j) a second support arm (42) extending radially outwardly from one end of the second support cylinder, remote from the base plate, and mounting an X-ray tube unit (40),
   (k) a third wormwheel (43) provided on another, opposite end of the second support cylinder,
   (l) the sample table, the X-ray detector unit and the X-ray tube unit being substantially coplanar, and
   (m) first, second and third wormgear drive means (28,38,49) individually engaged with the first, second and third wormwheels for independently rotating the sample table, the X-ray detector unit and the X-ray tube unit about a common central axis defined by the shaft.

2. A goniometer according to claim 1, further comprising a side plate (13) fixed to an edge of the base plate and extending parallel to said central axis, and hinge means (16) mounting said edge to a support base such that the goniometer can be rotated 90° about the hinge means between an orientation whereat the central axis is vertical and an orientation whereat the central axis is horizontal.

* * * * *